United States Patent [19]

Inaba et al.

[11] Patent Number: 5,331,961
[45] Date of Patent: Jul. 26, 1994

[54] SCINTILLATION PROBE AND INTRA-TUBE CAVITY INSERTABLE RADIOACTIVE RAY DETECTING APPARATUS

[75] Inventors: Makoto Inaba, Hino; Masakazu Gotanda, Kanagawa; Hiromu Takahashi, Sendai; Takashi Nakamura, Sendai; Masatoshi Itoh, Sendai; Masaki Matsumoto, Sendai; Hiroshi Watabe, Sendai, all of Japan

[73] Assignee: Olympus Optical Co., Ltd., Tokyo, Japan

[21] Appl. No.: 853,622

[22] Filed: Mar. 19, 1992

[30] Foreign Application Priority Data

Jul. 3, 1991 [JP] Japan ..................... 3-163123

[51] Int. Cl.$^5$ .............................................. A61B 6/00
[52] U.S. Cl. ................................ 128/659; 128/653.1; 128/654; 250/367; 250/368
[58] Field of Search .................. 128/659, 653.1, 654; 250/368, 367, 366

[56] References Cited

U.S. PATENT DOCUMENTS

| | | |
|---|---|---|
| 3,665,916 | 5/1972 | Kobayashi et al. ................. 128/659 |
| 3,670,719 | 6/1972 | Kobayashi et al. ................. 128/659 |
| 4,186,307 | 1/1980 | Tanaka et al. ....................... 250/369 |
| 4,595,014 | 6/1986 | Barrett et al. . |
| 4,933,961 | 6/1990 | Rushbrooke et al. .............. 250/368 |
| 5,008,546 | 4/1991 | Mazziotta et al. ................... 250/367 |

FOREIGN PATENT DOCUMENTS

| | | | |
|---|---|---|---|
| 0160875 | 12/1980 | Japan ................................. 250/367 |
| 0168982 | 10/1983 | Japan ................................. 250/367 |

Primary Examiner—Lee S. Cohen
Assistant Examiner—Brian L. Casler
Attorney, Agent, or Firm—Armstrong, Westerman, Hattori, McLeland & Naughton

[57] ABSTRACT

In a probe, two scintillators are arranged in tandem, the front end surfaces of two optical fibers transmitting the light emitted by the scintillators are connected to the rear of the scintillators and two photoelectric converters converting the light to pulse signals are connected to the rear of the optical fibers. A gate delay generator produces a gate signal from one pulse signal. A delay amplifier delays the other pulse signal. An M.C.A. will count up in case the pulse signal output by the delay amplifier is obtained during the gate signal.

23 Claims, 8 Drawing Sheets

SCINTILLATION PROBE AND INTRA-TUBE CAVITY INSERTABLE RADIOACTIVE RAY DETECTING APPARATUS

FIELD OF THE INVENTION

This invention relates to scintillation probes and radioactive ray detecting apparatus and more particularly to a scintillation probe and intra-tube cavity insertable radioactive ray detecting apparatus which can be used in such narrow place as in a tube-cavity.

RELATED ART STATEMENT

The device utilizing radioisotopes (RI's) is used to know the position and shape of an organ, to locally diagnose such bad tumor as cancer and to know a vein circulating state by administering to a human body such various kinds of RI's as, for example, 131I, 198Au and 99mTc and measuring the radioactive rays from outside the body.

On the other hand, in order to detect a tumor within a body cavity, diagnosis using an endoscope is made with a naked eye. However, a minute tumor or a tumor below a mucous membrane is very difficult to detect even for a skilled operator.

Therefore, a process is used wherein a radioisotope (RI) to be accumulated on a tumor is administered, in which the radioactive rays discharged from the tumor are sensed with a radioactive ray detector inserted into the body cavity, so that tumors which can not be distinguished with an endoscope can be sensed. Now, in fact, as radioisotopes are scattered in tissues other than those of an objective tumor, such as from peripheral tissues, the radioactive rays will enter the detector to cause mis-sensing. Therefore, in order to make an effective sensing, it is necessary to detect only the radioactive rays discharged by the objective tumor.

In a conventional radioactive ray detecting apparatus using a scintillation detector or the like used as inserted into a body cavity, as in an imaging probe shown, for example, in U.S. Pat. No. 4,595,014, in order that the entrance direction of the radioactive rays entering the scintillator may be regulated to be a fixed direction, a collimator formed of such substance high in the radioactive ray shielding capacity as tungsten is arranged around the scintillator.

However, in the conventional radioactive ray detector using a collimator, in order to sufficiently shield the radioactive rays from the periphery, it is necessary for the collimator to have some volume (thickness) and it is necessary to increase the volume of the collimator as the intensity of the radioactive rays becomes higher.

Therefore, this conventional detector has the disadvantage that, in the case of detecting radioactive rays on a high level by limiting the incident direction, the radioactive ray detector will have to be so large that it cannot be inserted into a fine tube which is inserted within the body cavity of a living body.

OBJECTS AND SUMMARY OF THE INVENTION

An object of this invention is to provide a scintillation probe which can easily be inserted into a fine tube within the body cavity of a living animal and which has a sufficient directivity even for radioactive rays on a high level.

Another object of this invention is to provide an intra-tube cavity insertable radioactive ray detecting apparatus which can easily be inserted, is of a size insertable into a fine tube as exists within the body cavity of a living body, and which can detect even radioactive rays on a high level with a sufficient directivity.

Another object of this invention is to provide an intra-tube cavity insertable radioactive ray detecting apparatus which can easily be inserted, is of a size insertable into such a fine tube as exists within the body cavity of a living body, and which can detect a random coincidence of radioactive rays.

Briefly, the scintillation probe of this invention is a scintillation probe insertable into a tube cavity of a living body and comprises a plurality of scintillators emitting light by radioactive rays, a plurality of light transmitting means respectively carrying the light emitted by the above mentioned plurality of scintillators and a plurality of photoelectric converting means respectively receiving the light led by the plurality of light transmitting means for converting the light to electric signals.

In a preferred embodiment, the scintillation probe of the present invention comprises first and second scintillators, first and second light transmitting means and first and second photoelectric converting means and the first and second scintillators are arranged in tandem in the inserting direction.

In another preferred embodiment, the intra-tube cavity insertable radioactive ray detecting apparatus of the present invention comprises the scintillation probe mentioned above and a counting means making the signal output by the above mentioned first photoelectric converting means a gate signal and either simultaneously or anti-simultaneously counting the signal output by the second photoelectric converting means by using the above mentioned gate signal.

The other features and advantages of the present invention will become apparent with the following detailed explanation.

DETAILED DESCRIPTION OF THE PREFERRED EMBODIMENTS

The embodiments of the present invention shall be explained in the following with reference to the drawings.

Figure 1:
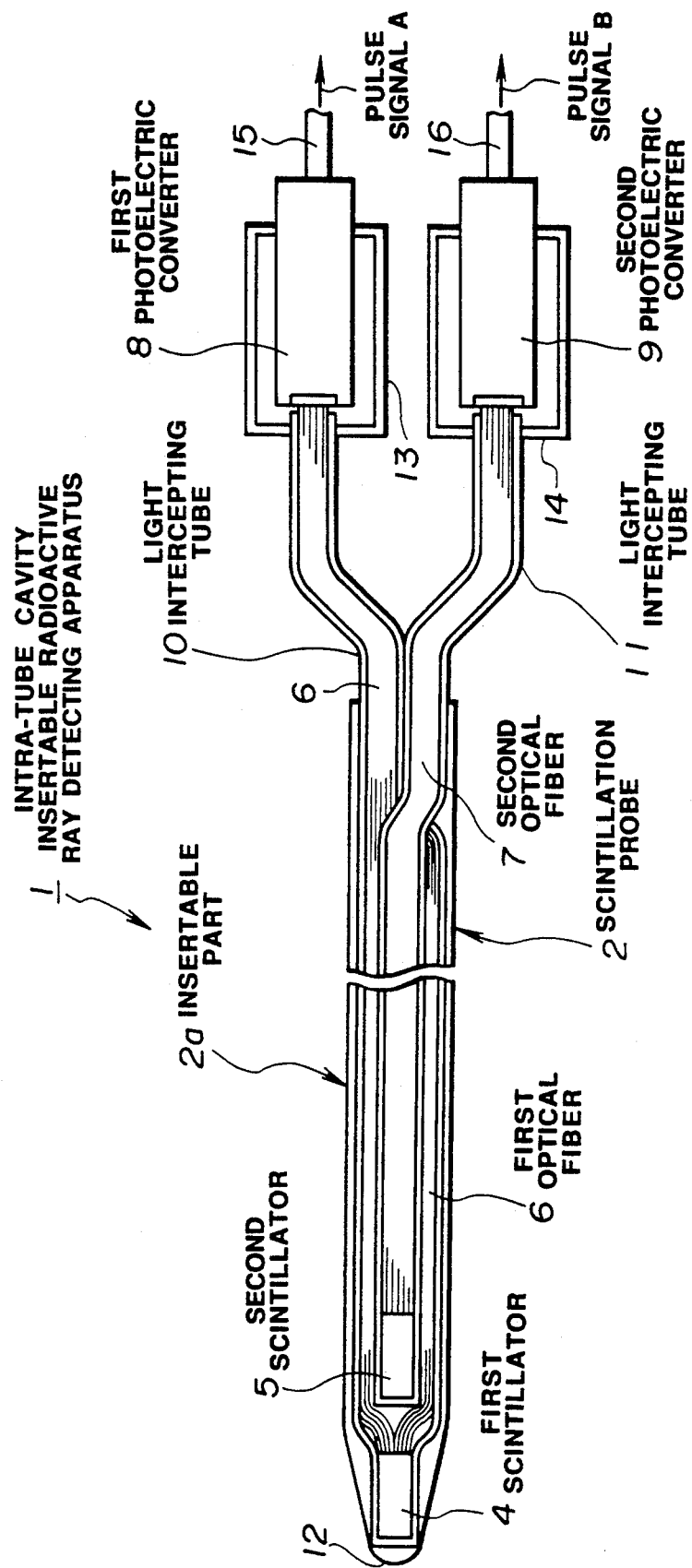
FIG. 1 is a sectioned view of a scintillation probe according to the first embodiment.
Figure 2:
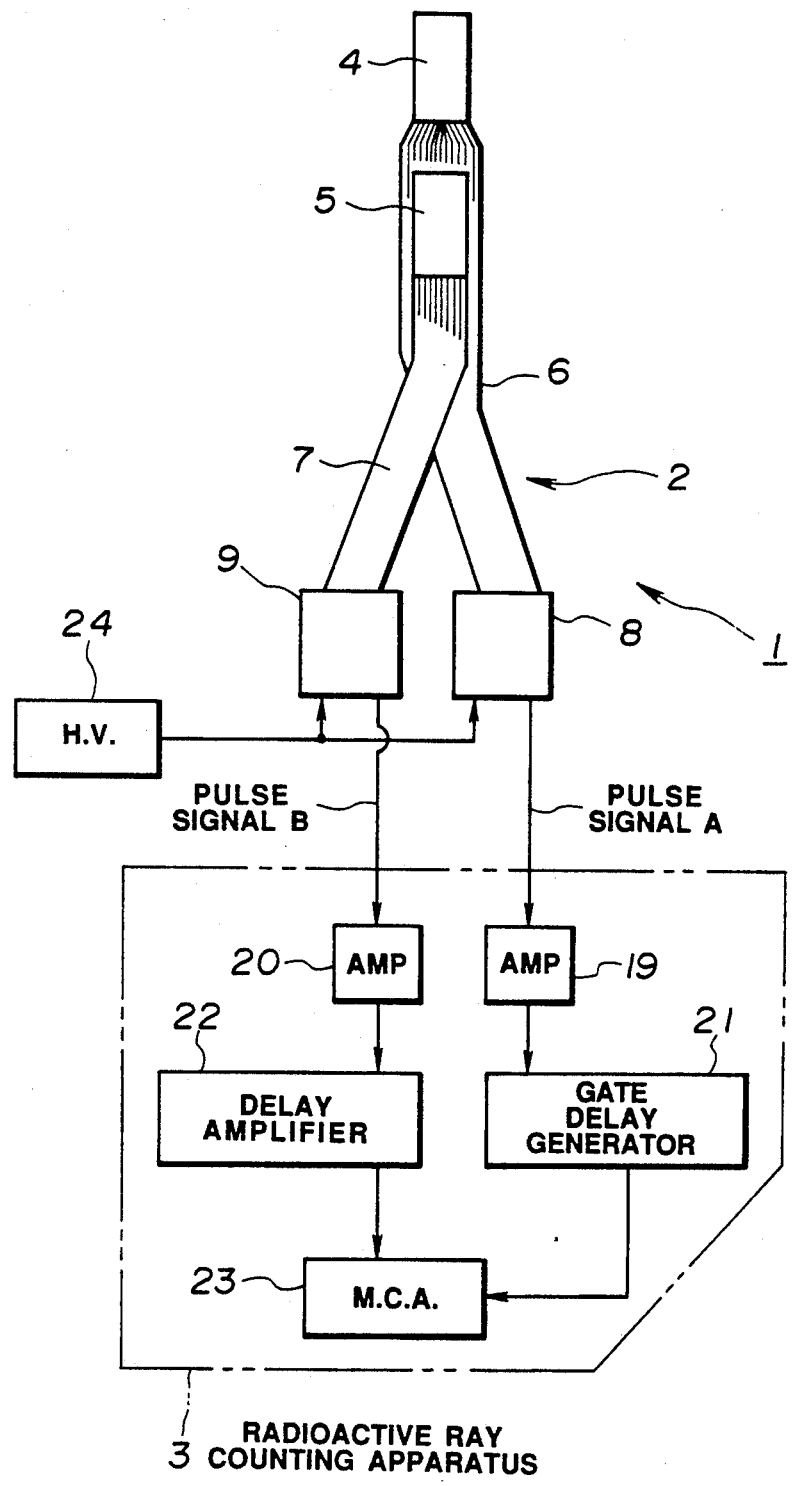
FIG. 2 is a general block diagram of an intra-tube cavity insertable radioactive ray detecting apparatus according to the first embodiment.
Figure 4:
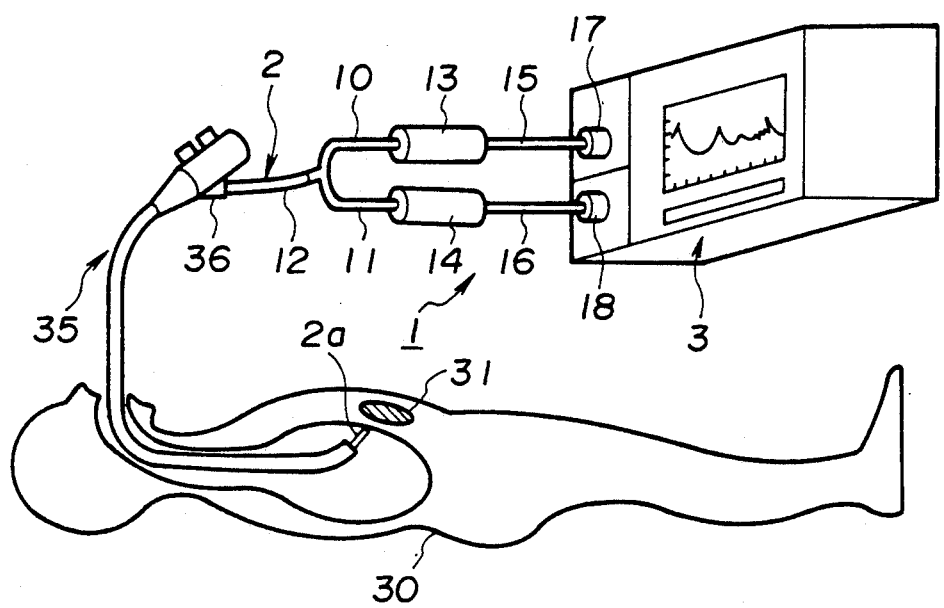
FIG. 4 is an explanatory view showing a using example of an intra-tube cavity insertable radioactive ray detecting apparatus.

An intra-tube cavity insertable radioactive ray detecting apparatus 1 shown in FIGS. 1, 2 and 4 comprises a scintillation probe 2 and radioactive ray counting apparatus 3. This intra-tube cavity insertable radioactive ray detecting apparatus 1 is to sense an affected part 31 by administering a predetermined radioisotope to a living body 30 and detecting radioactive rays discharged by an affected part 31 such as, for example, a tumor from within a tube cavity of the living body 30.

As shown in FIGS. 1 and 4, the scintillation probe (mentioned as the probe hereinafter) 2 of the intra-tube cavity insertable radioactive ray detecting apparatus 1 has an insertable part 2a insertable into a tube cavity of the living body 30 and is inserted into the living body to detect radioactive rays from the living body tissue.

Figure 3:
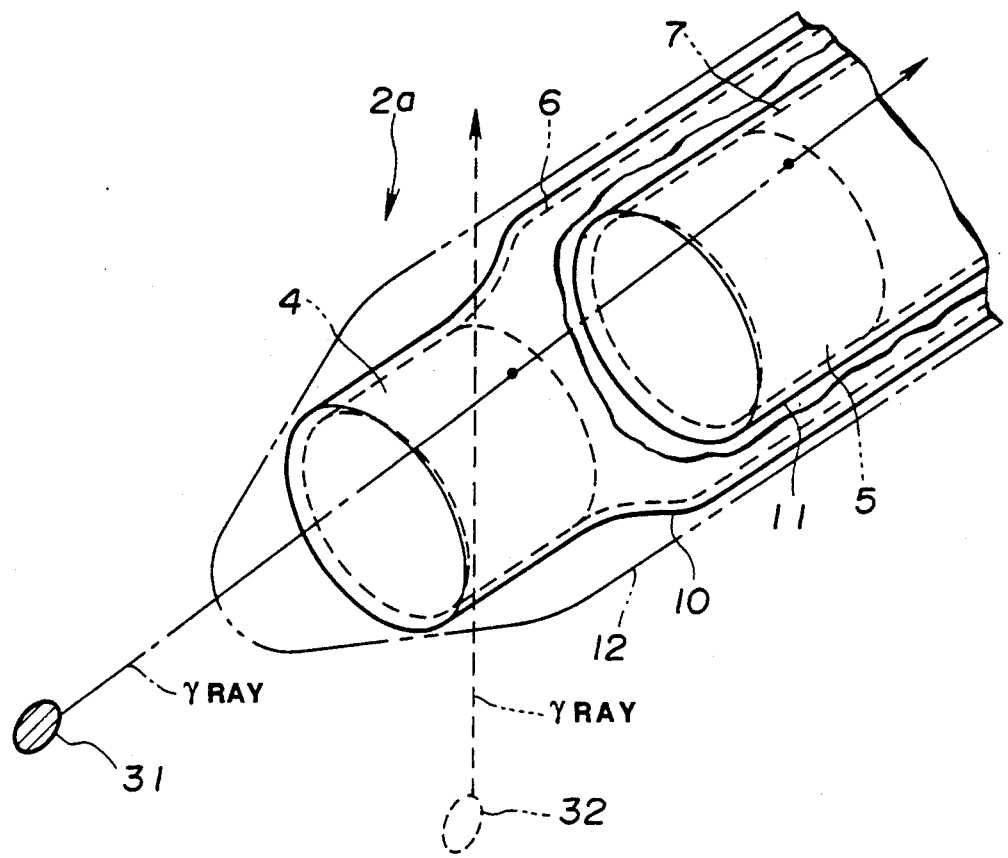
FIG. 3 is a tip formation view of a scintillation probe according to the first embodiment.

As shown in FIGS. 1 and 3, the insertable part 2a of the probe 2 extends in a longitudinal axial direction, and has first and second scintillators 4 and 5 emitting light in response to the incidence of radioactive rays thereon and which are arranged adjacent to the tip side interior and in tandem in the axial direction of the tip of the probe 2 (i.e., the inserting direction). The first and second scintillators 4 and 5 are formed to be respectively cylindrical. The first scintillator 4 is arranged to be more on the tip side than the second scintillator 5 and so that the circular surfaces of the cylinders may be opposed to each other. The shape of the scintillator is not limited to a cylindrical shape but, for insertability, it is desirable to be cylindrical.

The front end surfaces of the first and second optical fibers 6 and 7 are light transmitting means transmitting respectively the light emitted by the respective scintillators 4 and 5. The optical fibers 6 and 7 are connected respectively to the rear end surfaces of the first and second scintillators 4 and 5. The first and second optical fibers 6 and 7 carry the light emitted by the scintillators 4 and 5 respectively to rear end surface sides of the optical fibers 6 and 7. First and second photoelectric converters 8 and 9 are photoelectric converting means receiving respectively the light emitted by the scintillators 4 and 5. The converters 8 and 9 convert the received light to electric pulse signals, and are connected respectively to the rear end surfaces of the first and second optical fibers 6 and 7. Hereinafter, the electric signal output by the first photoelectric converter 8 shall be called a pulse signal A and the electric signal output by the second photoelectric converter 9 shall be called a pulse signal B.

As shown in FIG. 1, the section from the front surface of the second scintillator 5 to the rear end side of the second optical fiber 7 is covered with a light intercepting tube 11 as a soft light intercepting means closed on the tip side of the scintillator 5. Also, the first optical fiber 6 is formed to uniformly enclose the outer periphery of the above mentioned light intercepting tube 11 in the section from the second scintillator 5 to the midway of the second optical fiber 7. Further, the section from the front surface of the first scintillator 4 to the rear end side of the first optical fiber 6 is covered with the light intercepting tube 10 as a soft light intercepting means closed on the tip side of the scintillator 4. Therefore, the light emitted by the respective scintillators 4 and 5 will not leak out, will respectively enter the photoelectric converters 8 and 9, and external light will be prevented from entering the photoelectric converters 8 and 9.

Further, the first and second scintillators 4 and 5 and the first and second optical fibers 6 and 7 are inserted through a soft sheath formed to be round and closed on the tip side to form the above mentioned insertable part 2a. It is desirable that this sheath 12 be formed of light blocking materials.

The above mentioned sheath 12, is formed to cover the first and second scintillators 4 and 5, which are covered with the light intercepting tubes 10 and 11, and the sheath 12 extends to about midway along the length of the first and second optical fibers 6 and 7 so as to make them integral and to improve the insertability. Also, the section from about midway of the first and second optical fibers 6 and 7 to the rear end side thereof is separated so that the optical fibers 6 and 7 can be connected respectively to the above mentioned first and second photoelectric converters 8 and 9.

When, as described above, the optical fiber 7 is formed to be enclosed with the optical fiber 6 and is formed integrally with the light intercepting tubes 10 and 11 and the sheath 12, a soft and elongate insertable part 2a which has a high insertability can be formed.

The rear end part sides of the first and second optical fibers 6 and 7 covered with the respective light intercepting tubes and the first and second photoelectric converters 8 and 9 are covered respectively with light intercepting cases 13 and 14 to prevent the incidence of external light.

As shown in FIG. 4, signal cables 15 and 16 electrically transmitting pulse signals A and B are connected respectively to the rear end sides of the first and second photoelectric converters 8 and 9 and are connected through removable connectors 17 and 18 to the above mentioned radioactive ray counting apparatus 3 having a counting means built-in. As shown in FIG. 2, the first and second photoelectric converters 8 and 9 are connected respectively to amplifiers 19 and 20 through the signal cables 15 and 16. By the way, the reference numeral 24 represents a high voltage power source (H. V.) feeding a high voltage to the photoelectric converters 8 and 9.

The above mentioned amplifier 19 amplifies the pulse signal A and outputs it to the gate delay generator 21 which delays the pulse signal A and outputs a gate signal of a predetermined time width to a multi-channel analyzer (briefly mentioned as an M.C.A. hereinafter) 23. Also, the gate delay generator 21 can obtain a gate signal in which the time width of the gate signal obtained from the pulse signal A is greatly delayed by varying the delay time and can output this gate signal to the M.C.A. 23.

The above mentioned amplifier 20 amplifies the pulse signal B and outputs it to the delay amplifier 22 which delays the pulse signal B to make a simultaneous counting measurement with the pulse signal A and outputs it to the above mentioned M.C.A. 23.

Only in the case where the pulse signal B output by the delay amplifier 22 is obtained during the gate signal output by the gate delay generator 21, the M.C.A. 23 count up. That is to say, the M.C.A. 23 will simultaneously count the pulse signals A and B. Therefore, in case radioactive rays are incident from the front, they will substantially simultaneously enter the first and second scintillators 4 and 5 and therefore the M.C.A. 23 will count up.

When the M.C.A. 23 obtains a gate signal very long in time width by the gate delay generator 21, a random coincidence will be measured, that is to say, background radiation can be measured. The M.C.A. 23 will obtain a value of the measured value obtained by the above described ordinary count less the background.

The operation of this embodiment shall be explained with reference to the drawings.

As shown in FIG. 3, in case an objective inspected part 31 is positioned in front of the scintillation probe 2, when the radioactive rays (for example, γ rays) enter the first scintillator 4, the radioactive rays having a straight advancing property will enter also the second scintillator 5. Light will be emitted substantially simultaneously by the γ rays incident from the front side of the scintillators 4 and 5 and substantially simultaneous pulse signals A and B will be obtained by the photoelectric converters 8 and 9. A gate signal will be obtained by the gate delay generator 21 through the amplifier 19 from the pulse signal A. This gate signal will be input into the M.C.A. 23. The pulse signal B will pass through the amplifier 20 and delay amplifier 22 and will be input into the M.C.A. 23. At this time, while the gate signal is obtained, the pulse signal B will be also input and therefore the M.C.A. 23 will count up. Whenever the pulse signals A and B simultaneously enter the scintillators 4 and 5, they will be counted.

On the other hand, the γ rays discharged at an angle to the longitudinal axis of the probe 2 from a peripheral region 32 (shown by the broken line in FIG. 3) of the objective inspected part 31 will enter either one of the first and second scintillators 4 and 5. The obtained signal will be either one of the pulse signals A and B and therefore the M.C.A. 23 will not count. The probability of the pulse signals A and B appearing simultaneously will be so low as to be negligible in the event where the peripheral part 32 is a radioactive ray source positioned to the side as in FIG. 3.

In this embodiment, as the scintillators 4 and 5 are arranged in tandem, the direction in which the radioactive rays simultaneously enter the scintillators 4 and 5 will be on the front side of the probe 2 and the directivity of detecting the radioactive rays will be on the front side. As a gate signal is obtained by adding a predetermined delay amount to the pulse signal A and is measured simultaneously with the pulse signal B, the γ rays discharged out of the peripheral part 32 can be excluded and the radioactive rays can be detected with a sharp directivity.

Further, when the delay time of the pulse signal A is greatly delayed through the gate delay generator 21, the random coincidence is measured and the obtained background value is subtracted from the counted value obtained by the above mentioned simultaneous measurement, the radioactive rays discharged out of the objective part 31 can be measured selectively more than the radioactive rays discharged out of the other part, that is, more accurately with a sharp directivity.

Thus, in this embodiment, as no thick collimator is arranged around the scintillator, the insertable part 2a of the probe 2 can be made small, fine in diameter, and high in insertability and, by the arrangement and simultaneous measurement of the scintillators, the scintillators can have a high directivity.

As the insertable part 2a of the probe 2 can be made fine in diameter, as in the example shown in FIG. 4, the intra-tube cavity insertable radioactive ray detecting apparatus 1 of this embodiment can be used together with an endoscope 35. The insertable part 2a of the probe 2 can be inserted through a forceps channel not illustrated from a forceps inserting port 36 of the endoscope 35. Therefore, under the endoscope observation, the insertable part 2a of the probe 2 can be made to reach the approximate position of an objective part which can be probed with the radioactive ray detection. It can be inserted also into such fine tube cavity within a living body as a vein or bile duct.

Even if the signal of the first scintillator 4 is made a pulse signal B, the signal of the second scintillator 5 is made a pulse signal A and they are reversely used, the same effect will be obtained.

Figure 5:
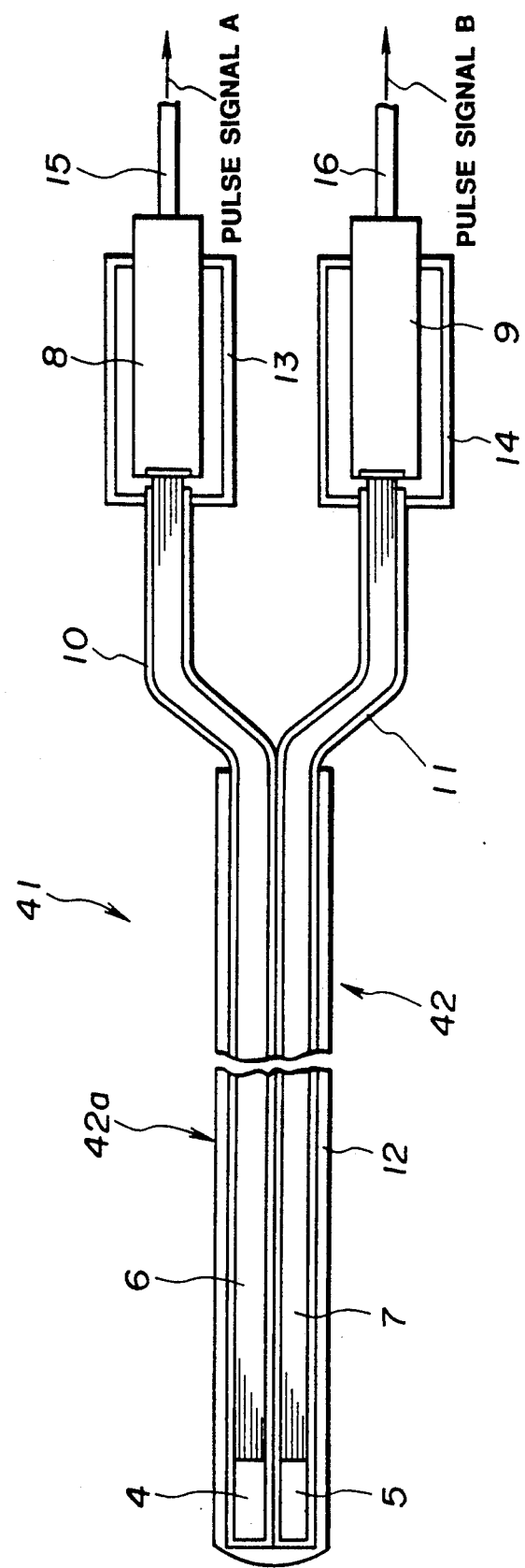
FIG. 5 is a sectioned view of a scintillation probe according to the second embodiment.
Figure 6:
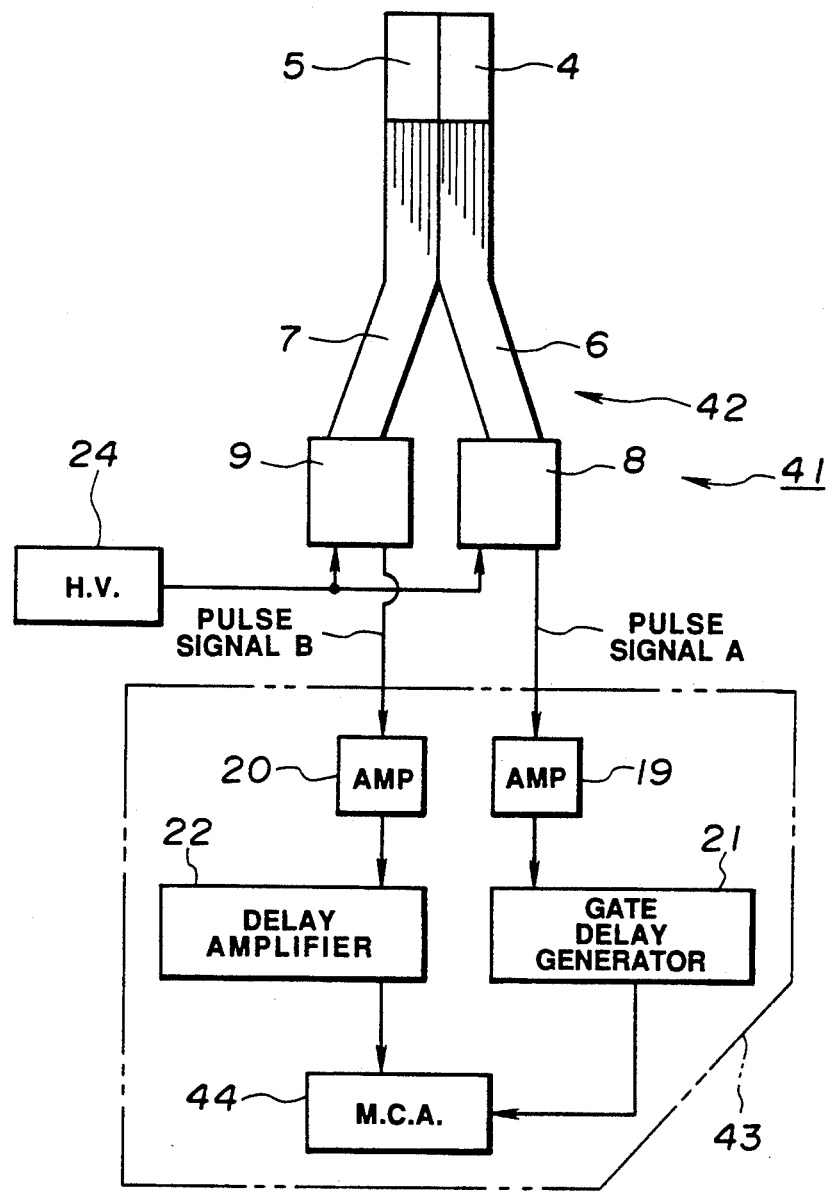
FIG. 6 is a general block diagram of an intra-tube cavity insertable radioactive ray detecting apparatus according to the second embodiment.

FIGS. 5 and 6 relate to the second embodiment of the present invention. FIG. 5 is a sectioned view of a scintillation probe. FIG. 6 is a general block diagram of an intra-tube cavity insertable radioactive ray detecting apparatus.

In this second embodiment, the scintillators 4 and 5 are arranged side by side as different from the first embodiment in which the scintillators 4 and 5 are arranged in tandem. The other same formations and operations as in the first embodiment shall bear the same reference numerals and shall not be explained here.

As shown in FIG. 5, in the intra-tube cavity insertable radioactive ray detecting apparatus 41, on the tip side of a scintillation probe (briefly mentioned as a probe hereinafter) 42, the scintillators 4 and 5 are arranged side by side and the optical fibers 5 and 6 are also parallelly provided in the axial direction. Therefore, the radioactive rays discharged out of the probe 42 in the forward direction will enter only either one of the scintillators 4 and 5. On the contrary, the radioactive rays discharged in another direction than the forward direction will substantially simultaneously enter the scintillators 4 and 5. That is to say, this probe 42 will have a directivity reverse to that of the first embodiment.

It is desirable in improving the insertability to form the two scintillators to be respectively semicylindrical so that a pair may be cylindrical. The two optical fibers can be formed in the same manner to improve the insertability.

On the other hand, when an M.C.A. 44 of a radioactive ray counting apparatus 43 shown in FIG. 6 is formed the same as the above mentioned M.C.A. 23, the radioactive rays discharged in another direction than the forward direction, that is, in the sidewise direction of the scintillators 4 and 5 will be able to be detected.

Or else, in case the directivity of the radioactive ray detection is made a forward direction, when the radioactive rays are made to simultaneously enter the scintillators 4 and 5 by the M.C.A. 44, the obtained count value will show a background. Therefore, in this apparatus, the background can be measured also in advance.

The apparatus of the second embodiment can be used also as an anti-simultaneous counter to exclude the background. That is to say, in case it is used as an anti-simultaneous counter, when the radioactive rays are simultaneously detected by the scintillators 4 and 5 arranged side by side, the anti-simultaneous counter will be able to be made to operate to prevent the count, for example, in the M.C.A. 23 of the apparatus 1 (main detector) of the first embodiment.

Further, as a third embodiment, there is possible an intra-tube cavity insertable radioactive- ray detecting apparatus wherein the scintillators 4 and 5 arranged side by side of the second embodiment are combined with the scintillators 4 and 5 arranged in tandem of the first embodiment to make a simultaneous count and anti-simultaneous count.

In the third embodiment, there is used a probe wherein, in at least one of the scintillators 4 and 5 arranged in tandem of the first embodiment, a guarding scintillator formed like a ring to enclose this scintillator on the outer periphery is arranged or a probe wherein the same guarding scintillators 4 and/or 5 as of the second embodiment are arranged side by side so that a simultaneous count may be made by the scintillators 4 and 5 arranged in tandem and, on the other hand, an anti-simultaneous count may be made by the scintillator 4 or 5 and the guarding scintillator. For example, in case the radioactive rays substantially simultaneously enter the scintillators 4 and 5 arranged in tandem and the guarding scintillator, the count value by the scintillators 4 and 5 arranged in tandem will be prevented. This apparatus can make the directivity of the radioactive ray detection sharper than by the apparatus of the first and second embodiments.

Figure 7:
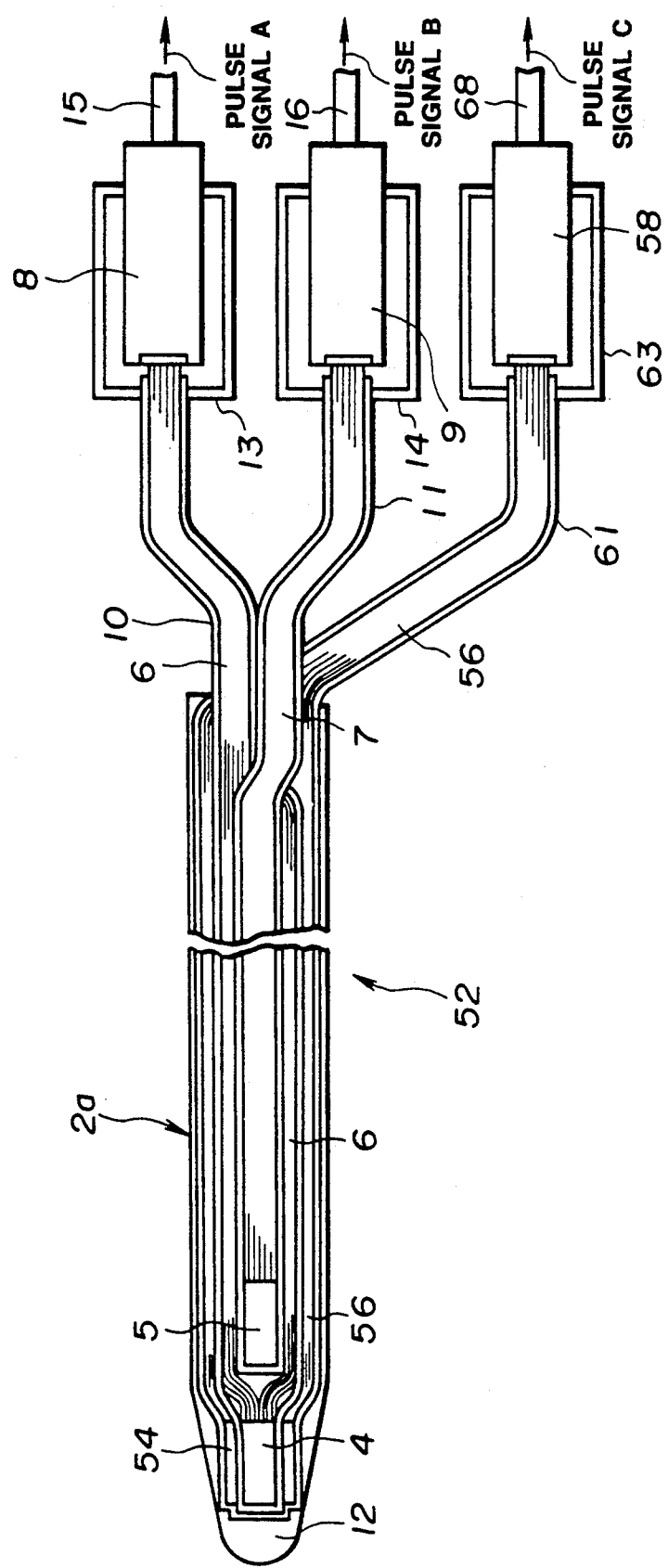
FIG. 7 is a sectioned view of a scintillation probe according to the third embodiment.
Figure 8:
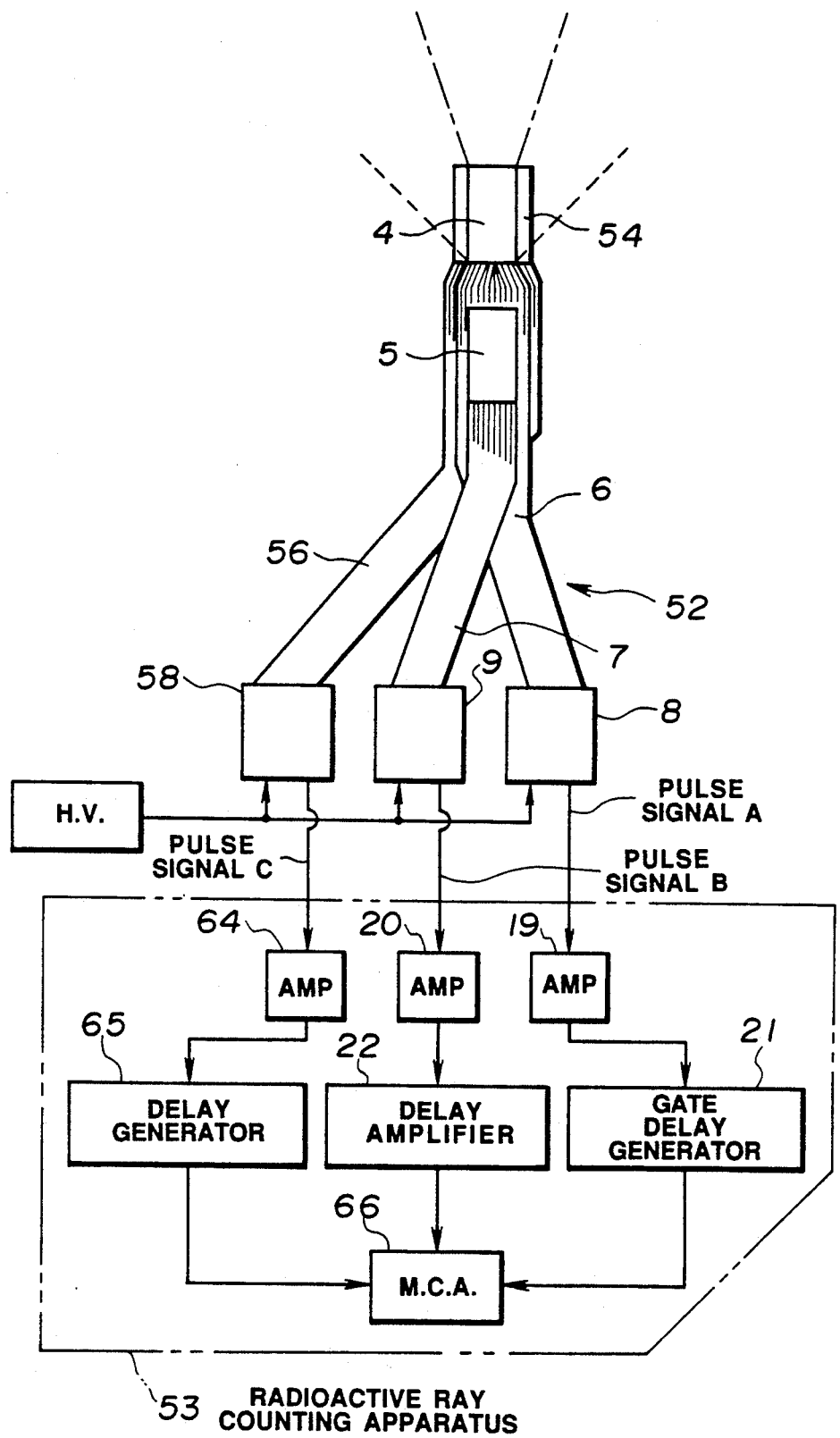
FIG. 8 is a general block diagram of an intra-tube cavity insertable radioactive ray detecting apparatus according to the third embodiment.
Figure 9:
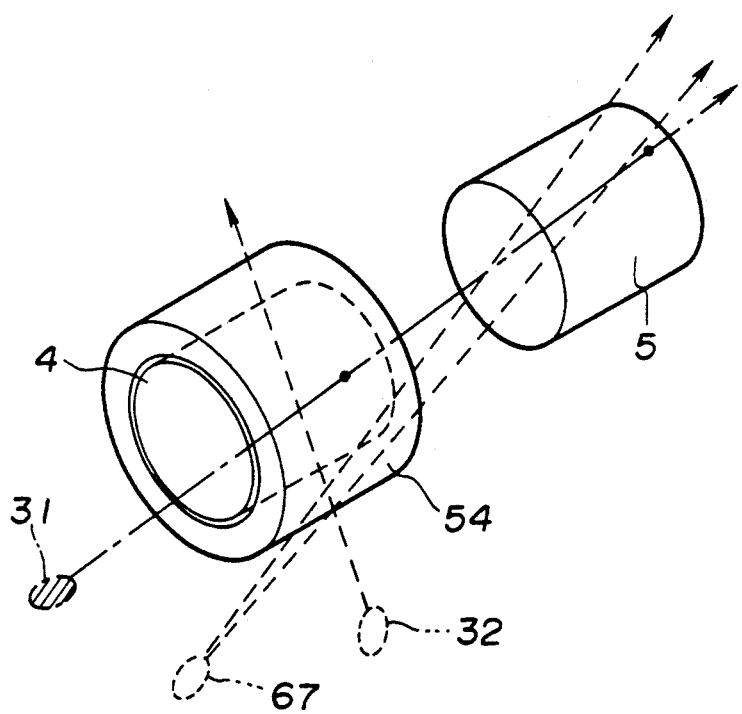
FIG. 9 is an explanatory view showing the arrangement of a scintillator according to the third embodiment.

A concrete example of the third embodiment is shown in FIGS. 7 to 9. FIG. 7 is a sectioned view of a scintillation probe. FIG. 9 is an explanatory view showing the arrangement of scintillators within a probe. FIG. 8 is a block diagram of an intra-tube cavity insertable radioactive ray detecting apparatus.

In a scintillation probe 52 shown in FIGS. 7 and 9 is arranged a guarding third scintillator 54 formed to be like a ring to enclose the scintillator 4 on the outer periphery of the scintillators 4 and 5 arranged in tandem of the first embodiment. The front end surface of a third optical fiber 56 transmitting the light emitted by the scintillator 54 is connected to the rear end surface of the guarding scintillator 54. A third photoelectric converter 58 receiving the light emitted by the scintillator 54 is connected to the rear end surface of the third optical fiber 56. The signal output by this third photoelectric converter 58 shall be called a pulse signal C hereinafter.

As shown in FIG. 7, the section from the front surface of the guarding scintillator 54 to the rear end side of the third optical fiber 56 is covered with a soft light intercepting tube 61 closed on the tip side of the scintillator 54. Also, the third optical fiber 56 is formed to uniformly enclose the above mentioned light intercepting tube 10 in the section from the first scintillator 4 to the midway of the first optical fiber 6. It is the same as in the first embodiment that the insertability is improved by such formation.

The rear end part side of the third optical fiber 56 and the third photoelectric converter 58 are covered with a light intercepting case 63 to prevent the incidence of external lights.

The same formations and operations as in the first embodiment shall bear the reference numerals and shall not be explained here.

An amplifier 64 of a radioactive ray counting apparatus 53 shown in FIG. 8 inputs a pulse signal C through the signal line 68 shown in FIG. 7, amplifies this pulse signal C and outputs it to a delay generator 65. The delay generator 65 delays the pulse signal C and outputs a gate inhibiting signal of a predetermined time width to a multi-channel analyzer (abbreviated as an M.C.A. hereinafter) 66.

The above mentioned M.C.A. 66 will count up only in case a pulse signal B output by the delay amplifier 22 is obtained during the gate signal output by the above mentioned gate delay generator 21. Also, the above mentioned M.C.A. 66 will inhibit the count up in case the pulse signal B output by the delay amplifier 22 is obtained while the gate inhibiting signal is obtained from the gate delay generator 21. That is to say, the M.C.A. 66 will make a simultaneous count only in case the pulse signals A and B are substantially simultaneously obtained (and the pulse signal C is not obtained) and, on the other hand, will make a non-simultaneous measurement preventing the count up in case not only the pulse signals A and B but also the pulse signal C are substantially simultaneously obtained.

Therefore, in this embodiment, not only the rays discharged out of the peripheral part 32 but also the γ rays discharged out of the peripheral part 67 can be excluded and the radioactive rays can be detected with a sharp directivity.

Here, in the apparatus of the first embodiment, the radioactive ray detecting directivity is within the broken lines (conical shape) shown in FIG. 8. On the other hand, in the third embodiment, the radioactive rays linearly incident from the region of the broken lines and one-point chain lines are an object of the above mentioned non-simultaneous measurement and therefore are not counted up. Therefore, the directivity of the apparatus of the third embodiment is within the one-point chain lines (conical shape) shown in FIG. 8. Thus, the apparatus of this embodiment can make the radioactive ray detecting directivity sharper than by the apparatus of the first embodiment.

The M.C.A. 66 is to obtain a value by excluding the background from the measured value obtained by the above described simultaneous count.

The other formations, operations and effects are the same as in the first embodiment and shall not be explained here.

In the third embodiment, the third scintillator 54 is arranged on the outer periphery of the first scintillator 4 but may be arranged as a modification on the outer peripheral side of the second scintillator 5. The other formations, operations and effects are the same as in the third embodiment and shall not be explained here. The directivity of this modification senses the radioactive rays from a wider region in the forward direction than in the third embodiment. That is to say, the directivity is dull.

Also, as a second modification of the third embodiment, the third scintillator 54 is arranged in tandem at the rear end of the second scintillator 5. The other formations, operations and effects are the same as in the third embodiment and shall not be explained. Whereas the directivity of the third embodiment and the modification can detect the radioactive rays from the rear direction the same as from the front direction of the one-point chain lines shown in FIG. 8, the directivity of this second modification does not detect the radioactive rays from the rear direction and can be held only in the front direction.

In the above mentioned first and third embodiments and the respective modifications, the directivity can be elevated by increasing the distance between the first scintillator 4 and the second scintillator 5 and by reducing the diameter of the scintillator.

Further, when the lengths in the inserting direction of the first and second scintillators 4 and 5 are made short, the difference between the directivities of the respective apparatus of the above mentioned first and third embodiments will be able to be made small.

In the above mentioned second embodiment, not only the arrangement of the scintillators 4 and 5 side by side but also, as a modification, such arrangement (formation except the scintillator 5) as of the scintillators 4 and 54 in FIG. 9 may be made. As the scintillation probe is otherwise of the same formations and operations as in the third embodiment, the drawings and explanation shall be omitted. Also, as the radioactive ray counting apparatus is of the same formations and operations as in the second embodiment, the drawings and explanation shall be omitted. In the second embodiment, in case the radioactive rays discharged, for example, from the side direction are simultaneously measured, the radioactive rays incident vertically to the paper surface in FIG. 5 will not be able to be detected. However, in this modification, the radioactive rays incident vertically from the outer peripheral side of the scintillator 54 can be also detected. The other formations, operations and effects are the same as in the second embodiment and shall not be explained here.

In this embodiment, it is apparent that working modes different in a wide range can be formed on the basis of the spirit of the invention. This invention is not restricted by its specific working modes except being limited by the appended claims.

What is claimed is:

1. A scintillation probe insertable into a tube cavity of a living body, comprising:
    an insertable portion extending in a longitudinal direction, said insertable portion having a tip portion;
    a plurality of scintillators disposed in said tip portion, shielded from external light, and positioned adjacent to each other, each of said plurality of scintillators individually emitting light in response to a detection of radioactive rays;
    a plurality of light transmitting means respectively connected to carry light emitted by each of said plurality of scintillators; and
    a plurality of photoelectric converting means receiving respectively the light carried by said plurality of light transmitting means, for converting the light to electric signals; and an analyzer means connected to an output of the photoelectric converting means to count the radiation emitted from the vicinity of the tip portion of the probe.

2. A scintillation probe insertable into a tube cavity of a living body, comprising:
    an insertable portion extending in a longitudinal direction, said insertable portion having a tip portion;
    first and second scintillators disposed in said tip portion, shielded from external light, and positioned adjacent to each other, each of said scintillators individually emitting light in response to a detection of radioactive rays;
    first and second light transmitting means respectively connected to carry light emitted by each of said first and second scintillators; and
    first and second photoelectric converting means receiving respectively the light carried by said first and second light transmitting means, for converting the light to electric signals; and an analyzer means connected to an output of the photoelectric converting means to count the radiation emitted from the vicinity of the tip portion of the probe.

3. A scintillation probe according to claim 2, wherein:
    said first scintillator and first light transmitting means are covered with a first light intercepting means which is closed on a side adjacent said tip portion for shielding said first light transmitting means from light; and
    said second scintillator and second light transmitting means are covered with a second light intercepting means which is closed on a side adjacent said tip portion for shielding said second light transmitting means from light.

4. A scintillation probe according to claim 3, further comprising a soft cover member, wherein:
    said first scintillator, said first light transmitting means, and said first light intercepting means, and said second scintillator, said second light transmitting means, and said second light intercepting means are integrally covered at least partly by said soft cover member, said soft cover member being closed to cover said tip portion.

5. A scintillation probe according to claim 2, 3, or 4, wherein said longitudinally extending tip portion extends along a longitudinal axis; and wherein:
    said first and second scintillators are arranged in tandem along said longitudinal axis of said tip portion.

6. A scintillation probe according to claim 5, wherein:
    said first and said second scintillators are cylindrical bodies having circular end faces, and are arranged in tandem along said longitudinal axis one of said circular end faces of said first scintillator is opposed to another one of said circular end faces of said second scintillator.

7. A scintillation probe according to claim 2, 3, or 4, wherein:
    said tip portion has an end;
    said first scintillator has a front side and a rear side, and is disposed adjacent said tip portion such that said front side faces said end of said tip portion;
    said second scintillator is arranged in tandem adjacent said rear side of said first scintillator; and
    said first light transmitting means encloses uniformly an outer peripheral surface of said second light intercepting means covering the second scintillator and said second light transmitting means.

8. An intra-tube cavity insertable radioactive ray detecting apparatus according to claim 2, 3 or 4, wherein:
    said first scintillator is cylindrical; and
    said second scintillator is ring-shaped and is coaxially disposed on an outer periphery of said first scintillator.

9. A scintillation probe according to claim 3, wherein:
    said first and second scintillators are arranged side by side in a direction along said longitudinal axis.

10. An intra-tube cavity insertable radioactive ray detecting apparatus, comprising:
    an insertable portion extending in a longitudinal direction, said insertable portion having a tip portion;
    first and second scintillators disposed in said tip portion, shielded from external light, each of said scintillators individually emitting light in response to detection of radioactive rays;
    first and second light transmitting means respectively connected to carry light emitted by each of said first and second scintillators; and
    first photoelectric converting means and second photoelectric converting means receiving respectively the light carried by said first and second light transmitting means, for converting the light to electric signals; an output signal of said first photoelectric converting means constituting a gate signal;

a counting means responsive to said output of said first photoelectric converting means, for performing either one of a synchronous count and an asynchronous count with output signal from said second photoelectric converting means by using said gate signal.

11. An intra-tube cavity insertable radioactive ray detecting apparatus according to claim 10, wherein said counting means comprises: a gate delay generator connected to said first photoelectric converting means and producing said gate signal obtained by adding a delay amount to the signal output by said first photoelectric converting means;

a delay amplifier connected to said second photoelectric converting means and delaying the signal output by said second photoelectric converting means; and a multi-channel analyzer means receiving the output signals from said first and second photoelectric converting means, for carrying out either one of a synchronous count and an asynchronous count with the signal output by said delay amplifier by using said gate signal produced by said gate delay generator.

12. An intra-tube cavity insertable radioactive ray detecting apparatus according to claim 10, wherein said counting means comprises:

a gate delay generator connected to said first photoelectric converting means, said gate delay generator producing said gate signal obtained by adding a delay amount to said signal output by said first photoelectric converting means; and a delay amplifier connected to said second photoelectric converting means, said delay amplifier delaying said signal output by said second photoelectric converting means;

wherein only a random coincidence is measured by using said gate signal produced by said gate delay generator.

13. An intra-tube cavity insertable radioactive ray detecting apparatus according to claim 12, wherein said counting means produces said gate signal by adding a delay amount which is larger than a delay produced by said delay amplifier in response to said signal output by said first photoelectric converting means by said gate delay generator, for measuring only a random coincidence measured by using said gate signal produced by said gate delay generator.

14. An intra-tube cavity insertable radioactive ray detecting apparatus according to claim 13, wherein said counting means comprises a multi-channel analyzer means for counting said signal output by said delay amplifier in response to said delay signal wherein a large delay amount is added by said gate delay generator, for measuring only a random coincidence by using said gate signal produced by said gate delay generator.

15. An intra-tube cavity insertable radioactive ray detecting apparatus according to claim 14, wherein:

said multi-channel analyzer means produces a value obtained by excluding said count of only said random coincidence from said count value by said simultaneous count with said signal output by said delay amplifier.

16. A scintillation probe insertable into a tube cavity of a living body, comprising:

an insertable portion extending in a longitudinal direction, said insertable portion having a tip portion;

first, second, and third scintillators disposed in said tip portion, each shielded from external light, and positioned adjacent to each other, each of said first, second, and third scintillators individually emitting light in response to a detection of radioactive rays;

first light transmitting means, second light transmitting means, and third light transmitting means respectively connected to carry light emitted by each of said first, second, and third scintillators; and first, second, and third photoelectric converting means receiving respectively the light carried by said first, second, and third light transmitting means, for converting the light to electric signals.

17. A scintillation probe according to claim 16, wherein:

said first scintillator and said first light transmitting means are covered with a first light intercepting means closed on a side facing said tip portion for shielding said first scintillator and said first light transmitting means from external light;

said second scintillator and said second light transmitting means are covered with a second light intercepting means closed on a side facing said tip portion for shielding said second scintillator and said second light transmitting means from external light; and said third scintillator and said third light transmitting means are covered with a third light intercepting means closed on a side facing said tip portion for shielding said third scintillator and said third light transmitting means from light.

18. A scintillation probe according to claim 17, further comprising a soft cover member, and wherein:

said first, second, and third scintillators, said first, second, and third light transmitting means, and said first, second, and third light intercepting means are integrally covered at least partly with said soft cover member closed on a side facing said tip portion, at an end of said tip portion.

19. A scintillation probe according to claim 18, wherein:

said first and second scintillators are cylindrical bodies having circular end faces, and are arranged in tandem along said longitudinal direction such that a circular end face of said first scintillator is opposed to a circular end face of said second scintillator;

said second scintillator is arranged on a rear end side of said first scintillator;

said third scintillator is ring-shaped and is coaxially disposed on an outer periphery of said first scintillator;

said first light transmitting means is arranged so as to uniformly peripherally enclose said second light intercepting means covering said second scintillator and said second light transmitting means; and said third light transmitting means is arranged so as to uniformly enclose in a peripheral direction said first light intercepting means covering said first scintillator and first light transmitting means.

20. An intra-tube cavity insertable radioactive ray detecting apparatus according to claim 18, wherein:

said first and second scintillators are cylindrical bodies having circular end faces, and are arranged in tandem along said longitudinal direction such that a circular end face of said first scintillator is opposed to a circular end face of said second scintillator;

said third scintillator is ring-shaped and is coaxially disposed on an outer periphery of either one of said first and second scintillators.

21. An intra-tube cavity insertable radioactive ray detecting apparatus according to claim 20, further comprising:
a counting means for converting said signal output by said first photoelectric converting means into a gate signal, for converting a synchronous count with said signal output by said second photoelectric converting means into a gate inhibiting signal, and for use together with said gate inhibiting signal for producing an asynchronous count.

22. An intra-tube cavity insertable radioactive ray detecting apparatus according to claim 21, further comprising:
a gate delay generator connected to said first photoelectric converting means and producing a gate signal obtained by adding a delay amount to said signal output by said first photoelectric converting means;
a delay amplifier connected to said second photoelectric converting means and delaying said signal output by said second photoelectric converting means;
a delay generator connected to said third photoelectric converting means and producing a gate inhibiting signal obtained by adding a delay amount to said signal output by said third photoelectric converting means; and
a multi-channel analyzer means receiving the output signals from said first and second photoelectric converting means and from said delay generator, for producing a simultaneous count with said signal output by said delay amplifier using said gate signal produced by said gate delay generator, and producing an asynchronous count while preventing said synchronous count by using said gate inhibiting signal produced by said delay generator prior to said synchronous count.

23. An intra-tube cavity insertable radioactive ray detecting apparatus according to claim 20, further comprising:
a counting means for converting said signal output by said first photoelectric converting means into a gate signal, for converting a synchronous count with said signal output by said second photoelectric converting means into a gate inhibiting signal, and for use together with said gate inhibiting signal for producing an asynchronous count a multi-channel analyzer means receiving the output signals from said first and second photoelectric converting means and from said delay generator, for producing a simultaneous count with said signal output by said delay amplifier using said gate signal produced by said gate delay generator, and producing an asynchronous count while preventing said synchronous count by using said gate inhibiting signal produced by said delay generator prior to said synchronous count;
wherein said multi-channel analyzer means produces a value obtained by excluding said count value of only a random coincidence from said count value of said synchronous count prior to which said asynchronous count is made.

* * * * *